United States Patent [19]

Vaudreuil

[11] 4,400,878
[45] Aug. 30, 1983

[54] KNIFE BLADE HOLDER

[75] Inventor: Richard E. Vaudreuil, Shrewsbury, Mass.

[73] Assignee: G & S Screw Machine Products, Inc., Worcester, Mass.

[21] Appl. No.: 308,477

[22] Filed: Oct. 5, 1981

[51] Int. Cl.³ .............................................. B26B 1/00
[52] U.S. Cl. ...................................... 30/329; 30/317; 30/336
[58] Field of Search ................. 30/329, 332, 335, 336, 30/314, 317

[56] References Cited

U.S. PATENT DOCUMENTS

| | | | |
|---|---|---|---|
| 2,507,872 | 5/1950 | Unsinger | 30/336 |
| 3,934,591 | 1/1976 | Gleason | 30/329 |

Primary Examiner—Robert C. Watson
Assistant Examiner—J. T. Zatarga
Attorney, Agent, or Firm—Blodgett & Blodgett

[57] ABSTRACT

A holder for an interchangeable knife blade comprising a handle, a chuck adapted to be threaded into the handle. The chuck has a bifurcated forward end defining a lengthwise slot for receiving a flat cutting blade, the bifurcated end defining a cam surface tapering outwardly toward the forward end to a major dimension. A tubular elastomeric ferrule is mounted on the chuck for longitudinal sliding movement relative to the chuck. The ferrule extends between the handle and the cam surface when the chuck is partially threaded into the bore, so that additional threading of the chuck into the bore causes the ferrule to slide forwardly over the cam surface. In this way, the forward end of the ferrule is stretched, thereby transmitting a clamping pressure against a blade which is located in the slot.

6 Claims, 5 Drawing Figures

U.S. Patent    Aug. 30, 1983    4,400,878
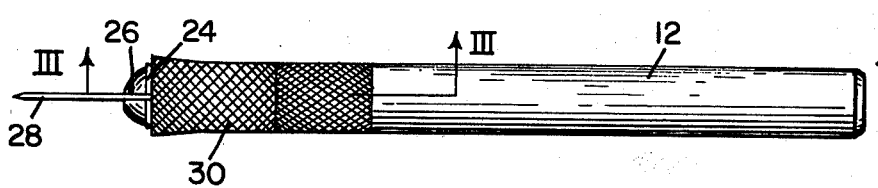
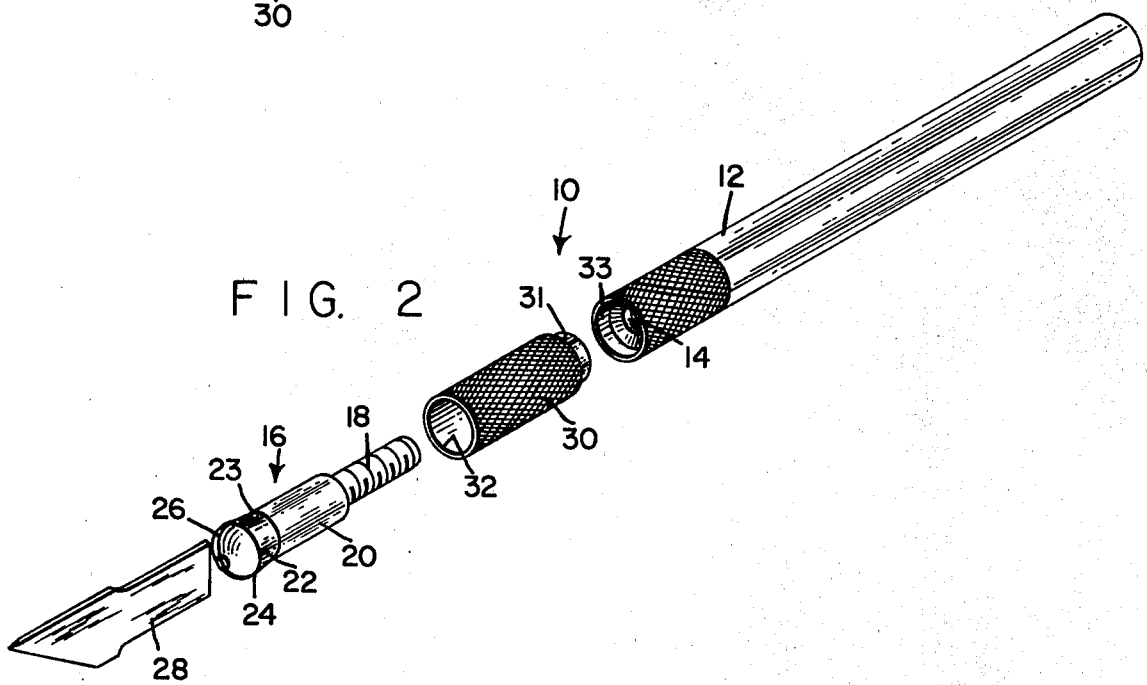
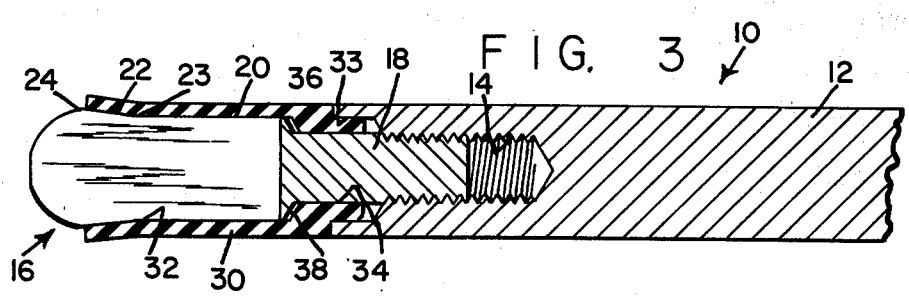
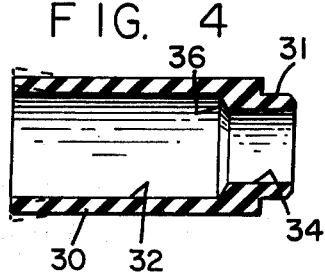
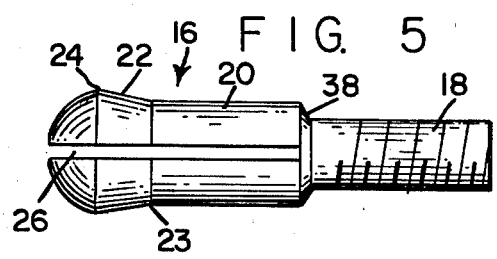

KNIFE BLADE HOLDER

BACKGROUND OF THE INVENTION

The present invention relates to a holder for an interchangeable knife blade, commonly referred to as a hobby knife, or utility knife. More specifically, the holder is of the type which has a blade-holding chuck with a longitudinal slot in one end for receiving a flat blade and with a threaded portion at the other end for threading into a handle. The slotted end of the chuck has a cam surface which flares outwardly toward the slotted end. A tubular ferrule is slidably mounted on the chuck between the handle and the cam surface. As the chuck is threaded into the handle, the ferrule is forced onto the cam surface, thereby closing the slot and clamping the blade which is located in the slot. Currently, blade holders of this type are made out of metal, particularly aluminum.

The present day hobby knives or utility knives as described above are extremely popular due to the fact that they are easy to use and are extremely versatile, so that they can be used for a wide range of applications. However, there are many problems associated with these knives. During use of the knife, any torque which is applied to the blade tends to unscrew the chuck, so that the blade becomes loose in the chuck. In order to prevent loosening of the blade, the chuck is screwed tighter into the handle and the ferrule tends to dig into the chuck. Eventually, the ferrule forges down the cam portion of the chuck, so that the ferrule can no longer be tightened. However, very often the ferrule splits before the chuck is completely forged down. These and other difficulties experienced with the prior art devices have been obviated by the present invention.

It is, therefore, an outstanding object of the invention to provide a blade holder which clamps a flat blade securely, so that it does not become loose during use.

Another object of the invention is the provision of a blade holder having a ferrule which will not split even after extensive use.

A further object of the present invention is the provision of a blade holder having a ferrule which will not dig into the chuck after an extended period of use.

It is another object of the instant invention to provide a blade holder in which the ferrule is made of a material which is elastic and yet is stiff enough to exert a high clamping pressure on the chuck.

A still further object of the invention is the provision of blade holder having means to prevent the ferrule from going beyond the major diameter of the cam portion of the chuck.

With these and other objects in view, as will be apparent to those skilled in the art, the invention resides in the combination of parts set forth in the specification and covered by the claims appended hereto.

SUMMARY OF THE INVENTION

In general, the invention consists of an interchangeable knife blade holder having a handle, a chuck threaded into the handle, and a tubular ferrule slidably mounted on the chuck. The forward end of the chuck is bifurcated to define a lengthwise slot for receiving a flat cutting blade. The chuck has a cam surface which tapers outwardly toward the forward end of the chuck to a major dimension. The ferrule is mounted on the chuck for longitudinal sliding movement and is elastic, so that, as the chuck is threaded into the handle, the ferrule is forced forwardly over the cam surface and is stretched as it approaches the major dimension of the cam surface so that it transmits a clamping pressure against a blade which is located in the slot.

More specifically, the blade holder includes stop means to prevent the ferrule from moving forwardly beyond the major dimension and the ferrule is formed of a stiff elastomeric thermoplastic material.

BRIEF DESCRIPTION OF THE DRAWINGS

The character of the invention, however, may be best understood by reference to one of its structural forms, as illustrated by the accompanying drawings, in which:

FIG. 1 is a plan view of the knife blade holder embodying the principles of the present invention, FIG. 2 is an exploded perspective view of the holder, FIG. 3 is a longitudinal sectional view, on an enlarged scale, of the holder taken along line III—III of FIG. 1, FIG. 4 is an enlarged longitudinal cross-sectional view of the ferrule, and FIG. 5 is an enlarged plan view of the chuck.

DESCRIPTION OF THE PREFERRED EMBODIMENT

Referring first to FIGS. 1 and 2, which best show the general features of the invention, the knife blade holder, indicated generally by the reference numeral 10, is shown as being of the type which can be disassembled for removal and insertion of interchangeable knife blades. The blades which are used with the holder are generally flat and have a standard shank portion which fits into the holder. However, the portions of the blades which extend from the holder have a wide range of shapes and cutting edges for a wide range of uses. The holder 10 includes a handle 12 which has a threaded bore 14 at its forward end. A chuck 16 has a reduced threaded portion 18 adapted to be threaded into the bore 14, an intermediate cylindrical portion 20, and a cam surface 22 at the forward end. The cam surface 22 is generally frusto-conical in shape and extends from a minor diameter 23 where it joins intermediate portion 12 and tapers outwardly in the forward direction to a major diameter 24. The forward end of the chuck is bifurcated to define a longitudinal slot 26 which extends from the front of the chuck 16 to the reduced threaded portion 18 for receiving a flat blade 28. The slot 26 is shown more clearly in FIG. 5. A cylindrical ferrule has a reduced end portion 31 which fits into a counterbore 33 in the forward end of the handle 12. The forward end of the ferrule 30 has a large diameter bore 32 and the rearward end of the ferrule has a small diameter bore 34 for receiving the chuck 20 in a sliding fit.

The ferrule 30 is made of a relatively stiff elastomeric material, so that, when the various elements of the knife blade holder 10 are assembled (as shown in FIG. 3), the forward end of the ferrule 30 extends about and embraces the cam surface 22 of the chuck. The diameter of the large diameter bore 32 is greater than the minor diameter 23, but is substantially less than the major diameter 24 of the cam surface 22. When the elements are in the assembled condition, as shown in FIG. 3, the forward end of the ferrule 22 is stretched, thereby applying a clamping force to the blade 28 which is located in the slot 26. It is essential that the ferrule 30 be made of a material having high elastomeric properties, yet the material must also be sufficiently stiff that, when it is stretched, it is able to exert considerable clamping pressure on the blade to hold it securely within the chuck 20. Certain thermoplastic materials known as acetals have been found to exhibit the qualities which are required for the proper functioning of the ferrule 30. Excellent results have been obtained from an acetal copolymer sold under the tradename Celcon which is a registered trademark of Celanese Plastics and Specialties Company, a division of Celanese Corporation. A ferrule made from this material exhibits stiffness, yet has a resiliency with spring-like recovery. In addition, after a long period of use, ferrules made from this material have exhibited toughness and a high fatigue endurance. Excellent results have also been obtained from holders made entirely from Celcon.

Referring particularly to FIGS. 3-5, the forward end of the ferrule 30 is prevented from moving past the major diameter 24 of the chuck 16 by stop means comprising a rearwardly facing external shoulder 38 on the chuck 16 and a forwardly-facing internal shoulder 36 within the ferrule 30.

The operation and advantages of the present invention will now be readily understood in view of the description. The knife blade holder 10 is assembled by inserting the reduced portion 31 of the ferrule 30 into the counterbore 33 of the handle 12. The chuck 16 is inserted through the ferrule 30, so that the threaded end 18 is partially threaded into the bore 14 of the handle. In this position the ferrule 30 is loosely mounted on the chuck and is free to slide longitudinally between the handle 12 and the cam surface 22. The blade 28 is then inserted into the slot 26 and the chuck is rotated about its longitudinal axis, so that the threaded end 18 is advanced further into the bore 14. This causes relative longitudinal movement between the chuck 16 and the ferrule 30, so that the forward end of the ferrule advances along the cam surface 22 and begins to stretch, thereby exerting a clamping pressure against the chuck 16 and forcing the biofurcated end of the chuck against the blade 28. As soon as the ferrule 30 begins to exert a gripping pressure on the chuck 16, the chuck may be advanced further into the handle 12 by simply grasping the outer surface of the ferrule. The outer surface of the ferrule 30 and the outer surface of the forward portion of the handle are preferably knurled to provide better gripping. This enables the user to grasp the handle at the forward end with one hand and to grasp the ferrule 30 with the other hand and rotate these two elements in opposite directions about the central longitudinal axis of the handle. This causes the chuck 16 to move deeper into the handle and causes the forward end of the ferrule 30 to advance toward the major diameter 24 of the chuck. However, the shoulder 38 of the chuck 16 eventually strikes the shoulder 36 of the ferrule 30 just before the forward end of the ferrule reaches the major diameter 24. This prevents the ferrule 30 from being pushed beyond the major diameter of the cam surface 22. It has been found that the ferrule provides sufficient clamping force on the blade before it reaches the major diameter 24. The use of an elastic ferrule has been found to be so effective in maintaining a tight grip on the blade that, even when the chuck 16 is partially unscrewed from the handle, the ferrule 30 remains in the gripping position on the chuck. In fact, it is removed from this position by gripping the surface of the ferrule and pulling it backward relative to the chuck, whereupon it moves away from the cam surface 22 with a snap. The blade 28 is removed by reversing the above-described procedure for insertion of a new or a different type of blade.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Holder for interchangeable knife blade, comprising:
   (a) a handle which has a threaded bore at one end,
   (b) a chuck which has a forward portion and a rearward portion, the rewarward portion being adapted for threading into said bore, the forward portion being bifurcated to define a lengthwise slot for receiving a flat cutting blade, said chuck having an external cam surface adjacent the forward end of said forward portion, said cam surface tapering outwardly toward said forward end to a major dimension, and
   (c) a tubular elastomeric ferrule mounted on the chuck for longitudinal sliding movement relative to the chuck, said ferrule extending between the handle and the cam surface when the chuck is partially threaded into the bore so that additional threading of the chuck into the bore causes the ferrule to slide forwardly over the cam surface, the inner dimension of said ferrule being substantially less than said major dimension, so that the ferrule is stretched as it approaches said major dimension, thereby transmitting a clamping pressure against a blade which is located in the slot.

2. Holder as recited in claim 1, wherein a stop means is provided to prevent the ferrule from moving forwardly beyond said major dimension.

3. Holder as recited in claim 2, wherein the stop means comprises:
   (a) a rearwardly facing external shoulder on the chuck, and
   (b) a forwardly facing internal shoulder within the ferrule adapted for engaging said external shoulder.

4. Holder as recited in claim 1, wherein the interior surface of the ferrule is cylindrical and the cam surface is frusto-conical.

5. Holder as recited in claim 1, wherein the ferrule is formed of an elastomeric thermoplastic material.

6. Holder as recited in claim 5, wherein said elastomeric thermoplastic material is acetal.

* * * * *